United States Patent [19]

Speaker et al.

[11] Patent Number: 5,132,117
[45] Date of Patent: Jul. 21, 1992

[54] AQUEOUS CORE MICROCAPSULES AND METHOD FOR THEIR PREPARATION

[75] Inventors: Tully J. Speaker, Philadelphia; Mani R. Sundararajan, Bryn Mawr, both of Pa.

[73] Assignee: Temple University, Philadelphia, Pa.

[21] Appl. No.: 463,339

[22] Filed: Jan. 11, 1990

[51] Int. Cl.$^5$ .............. B01J 13/16; A61K 9/50
[52] U.S. Cl. .................. 424/490; 264/4.1; 264/4.7; 428/402.2; 428/402.21; 424/493
[58] Field of Search ............ 264/4.1, 4.3, 4.7; 428/402.2, 402.21; 424/490, 493

[56] References Cited

U.S. PATENT DOCUMENTS

| | | | |
|---|---|---|---|
| 3,137,631 | 6/1964 | Soloway | 264/4.1 X |
| 3,201,353 | 8/1965 | Corben | 428/402.2 |
| 3,415,758 | 12/1968 | Powell et al. | 264/4.3 X |
| 3,959,457 | 5/1976 | Speaker et al. | 424/494 |
| 4,205,060 | 5/1980 | Monsimer et al. | 264/4.1 X |
| 4,277,364 | 7/1981 | Shasha et al. | 264/4.1 X |
| 4,324,683 | 4/1982 | Lim et al. | 264/4.3 |
| 4,606,940 | 8/1986 | Frank et al. | 514/400 |
| 4,608,278 | 8/1986 | Frank et al. | 427/213.35 |
| 4,744,933 | 5/1988 | Rha et al. | 264/4.3 |
| 4,789,516 | 12/1988 | Lim | 264/4.3 X |
| 4,797,234 | 1/1989 | Speaker et al. | 264/4.1 |

FOREIGN PATENT DOCUMENTS 1091077 11/1967 United Kingdom.
1091078 11/1967 United Kingdom.

OTHER PUBLICATIONS

Exploration of some major pharmaceutical Technologic Characteristics of Aqueous Core, Salt-walled Microcapsules, 1988, Mani Raj Sundararajan, thesis.

*Primary Examiner*—John S. Maples
*Assistant Examiner*—John M. Covert
*Attorney, Agent, or Firm*—Ratner & Prestia

[57] ABSTRACT

A microcapsule comprising an aqueous core, and capsular membrane formed from the interfacial reaction product of a hydrophilic polymeric Lewis acid or salt thereof with a lipophilic Lewis base or salt thereof.

31 Claims, No Drawings

5,132,117

AQUEOUS CORE MICROCAPSULES AND METHOD FOR THEIR PREPARATION

FIELD OF THE INVENTION

This invention relates to novel microcapsules having an anisotropic salt membrane encapsulating an aqueous or substantially aqueous core. The microcapsules are prepared by the interfacial reaction of Lewis acid and base wall-forming reactants.

BACKGROUND OF THE INVENTION

Microencapsulation is a process by which a relatively thin coating can be applied to dispersions of small particles of solids or droplets of liquids, thus providing a means for converting liquids to solids, altering colloidal and surface properties, providing environmental protection, and controlling the release characteristics or availability of coated materials. Several of these properties can be attained by macropackaging techniques; however, the uniqueness of microencapsulation is the smallness of the coated particles and their subsequent use and adaptation to a wide variety of dosage forms and product applications, which heretofore may not have been feasible technically.

INFORMATION DISCLOSURE STATEMENT

U.S. Pat. No. 3,137,631 relates to encapsulation of water insoluble organic liquids by cross-linking synthetic resins through the application of heat or catalysts or both. The capsule shells are described as formed from covalently linked non-ionic materials or from heat denaturable proteins. The resultant capsules benefit from secondary treatment with cross-linking agents to impart increased stability to the capsule.

U.S Pat. No. 4,205,060 discloses microcapsules comprising a core containing a water soluble salt formed by reaction between a polymeric ionic resin and a medicament, formed either by reaction of an acidic polymer with a basic medicament or, conversely, a basic polymer with an acidic drug. The walls of the microcapsules are formed from water-insoluble film-forming polymers. The water-insoluble film-forming polymers identified as suitable sheathing agents are all neutral non-ionized polymers. The capsules of that invention are made by preparing an aqueous solution of a salt made by reacting a medicament and a core polymer; preparing a solution of a water-insoluble sheath-forming polymer in a first water-immiscible organic liquid; dispersing the aqueous solution in the organic solution; and adding to the dispersion a second water-immiscible liquid which is a non-solvent for the sheath-forming polymer to precipitate the film around droplets of the dispersed aqueous phase.

U.S. Pat. No. 4,606,940 discloses the preparation of microcapsules by coacervation to precipitate the encapsulating material. A single colloid is dispersed in water and the water of solvation is removed from around the colloid by addition of chemical compounds which have a greater affinity for water than the colloid. This causes the colloid chains to come closer together and form the coacervate. Temperature changes are needed to facilitate the encapsulation by coacervation.

U.S. Pat. No. 3,959,457 discloses microcapsules comprised of the reaction product produced in a finely dispersed emulsion of a water-immiscible solution of (a) an organic polyfunctional Lewis base, in a (b) low boiling point, polar, organic solvent, and an aqueous solution of a (c) partially hydrophilic, partially lipophilic, polyfunctional Lewis acid. The capsules of that invention have lipophilic cores.

SUMMARY OF THE INVENTION

It is an object of this invention to provide stable microcapsules having aqueous cores. It is a further object of this invention to provide a high efficiency method of encapsulation.

The microcapsules of this invention consist of aqueous or substantially aqueous cores surrounded by capsular anisotropic Lewis salt membranes.

The aqueous-core microcapsules of this invention may be prepared by dispersing an aqueous solution of a suitable Lewis-acid wall-forming reactant and a core material in a suitable non-aqueous solvent, adding an additional amount of non-aqueous solvent containing a suitable Lewis-base wall-forming reactant, and harvesting the microcapsules formed by the interfacial reaction.

Alternatively, the aqueous-cored microcapsules of this invention may be prepared by dispersing an aqueous solution of a suitable Lewis-acid wall-forming reactant and a core material in a suitable non-aqueous solvent containing a suitable Lewis-base wall-forming reactant and harvesting the microcapsules formed by the interfacial reaction.

DETAILED DESCRIPTION OF THE INVENTION

In accordance with the first of the alternatives described above, the Lewis salt-walled aqueous-cored microcapsules of this invention are prepared by the general scheme described below. The capsular membrane is an ionically-stabilized, anisotropic Lewis salt membrane.

An aqueous solution of a suitable Lewis polyacid macromolecule or salt thereof is prepared. Suitable Lewis polyacids are polyfunctional electron pair acceptors including, but not limited to polyuronic acids and acidic resins, such as acacia, arabic acid, agar, carboxymethylcellulose, ghatti gum, guar gum, polyacrylic acid, polyacrylic acid/polyoxyethylene copolymer, and sterculia gum. Examples of Lewis polyacid salts are sodium carboxymethylcellulose, sodium polyacrylate, sodium polyacrylate cross-linked with polyoxyethylene, and sodium alginate. The choice of Lewis polyacid is a matter of preference and should be apparent to one skilled in the art. The acidic macromolecule must be water soluble. Typical concentrations of polyacid in water are from 1 to 20% by weight.

An aqueous solution or suspension of the desired core material is added to the aqueous solution of Lewis polyacid or salt prepared above. Alternatively, the desired core material is added directly to the Lewis polyacid solution. Both dissolved and suspended substances may be incorporated by the process of this invention provided that they do not interfere with the encapsulating process and do not react with or dissolve the capsular membrane. Effective amounts of core materials depend entirely on the type and characteristics of the core material, the capsular membrane thickness and on the intended utility of the product. Among the materials which have been encapsulated by the process of this invention are FD & C (Food, Drug and Cosmetic) Red No. 40, FD & C Red No. 1, doxorubricin hydrochloride, sodium fluorescein, sodium methotrexate, theophylline, deferoxamine, 5-fluorouracil, nicotinamide, terbutaline, and water.

A water-in-oil emulsifying agent, such as sorbitan trioleate, or a blend of emulsifying agents is dissolved in an organic solvent. The organic solvent, which may be a mixture, is selected from those solvents having a composite Hildebrand solubility parameter value of approximately 17 MPa$^{\frac{1}{2}}$, with the proviso that no single component be substantially miscible with water. An alternative criterion is that the solvent have Hildebrand-Hansen dispersion, dipole, and hydrogen bonding parameters of about 14, 15 and less than about 7 MPa$^{\frac{1}{2}}$, respectively, again with the proviso that no single component be substantially miscible with water. While the Hildebrand-Hansen values are useful tools in selecting organic solvents, the solvents must be tested as there are some which are not useful if selected on this basis alone. Some solvents and solvent combinations which have been found useful in the practice of this invention are set forth in Table 1 below:

TABLE 1

| SOLVENT & SOLVENT BLENDS | HILDEBRAND-HANSEN MPa$^{\frac{1}{2}}$ VALUES |
| --- | --- |
| n-Butyl chloride (neat) | 17.1 |
| Methyl isobutyl ketone (neat) | 17.6 |
| Cyclohexane (neat) | ≈16.8 |
| Dichloromethane & cyclohexane (1:4) | ≈17 |
| Hexane & n-heptane (1:1) | 15.1 |
| Cyclohexane & chloroform (4:1) | 17.2 |

Chloroform itself is another example of a solvent useful in this invention.

The aqueous solution o a Lewis polyacid or a suitable salt of a Lewis polyacid and core material is dispersed in the organic solvent containing the emulsifying agent, forming an emulsion. Generally, for each volume of aqueous solution, form 0.5 to 4.0 volumes of a 7% to 20% (by volume) emulsifying agent/organic solvent solution are used.

A suitable Lewis base or salt thereof is dissolved in the same organic solvent as used for preparation of the emulsion. Suitable Lewis bases include primary, secondary, and tertiary amines, bis-primary amines, and bis-secondary amines. Among the bases found useful in the practice of this invention are hexylamine, stearylamine, piperidine, triethylamine, hexanediamine, and triethylenediamine. Examples of suitable Lewis base salts are benzalkonium chloride, cetylpyridinium chloride, hexamethylrosanilium chloride, and tetramethylrosanilium chloride. Suitable Lewis bases and salts are not limited to those enumerated. Many Lewis bases are good wall-forming components, excepting those weakly basic compounds with high water solubility, such as tromethamine.

In general, any of the preferred free polyacids may be paired with any of the preferred free bases to form an effective pair of wall-forming reactants. Similarly, in general, any of the preferred salts of polyacids may be combined with any of the salts of bases to form a useful pair of wall-forming reactants. However, combining a free polyacid with the salt of a base or a free base with a salt of a polyacid generally results in lowered yields of finished microcapsules.

To form the microcapsules an amount of the Lewis base/organic solvent solution containing a stoichiometric amount of base equivalent to the amount of acid, is added to the acid/core material/water/organic solvent emulsion prepared above, while stirring vigorously. The resultant microcapsules are harvested by methods well known to those skilled in the art, as exemplified below.

It is convenient to centrifuge the suspension to speed separation of microcapsules from the phase comprising the non-aqueous solvent blend. The microcapsules may be separated more completely from the manufacturing fluid by a variety of means. The remaining non-aqueous solvent may be removed by volatilization, with or without the aid of externally applied heat or lowered pressure. Alternatively the remaining solution of surfactant in solvent blend may be removed by suspension of the microcapsule phase in a convenient diluting volume of cyclohexane or similar miscible solvent and harvesting, e.g. as by centrifugation, one or more times. The remaining solution of surfactant in non-aqueous solvent may be removed by both dilution and harvesting and volatilization; or any remaining unencapsulated aqueous solution may be removed by aspiration of the separated bulk aqueous phase; or any remaining unencapsulated aqueous phase may be removed by suspension of the microcapsule phase in a convenient diluting volume of water and harvesting, as by centrifugation, one or more times; or any remaining unencapsulated aqueous solution may be removed by aspiration of the separated bulk aqueous phase, suspension of the microcapsule phase in a convenient diluting volume of water and harvesting, as by centrifugation, one or more times.

Depending in part on the degree to which manufacturing fluid is removed and in part on the nature of the core solute, the aqueous core microcapsules may be collected as a free-flowing suspension, a viscid flowable concentrate, a paste, a friable flake or, with further treatment, as a lyocake. Lyophilization is particularly desired to provide stable microcapsules with highly water soluble core materials.

Under optimal conditions high efficiencies of encapsulation of the aqueous phase are obtained. These optimal conditions are dependent on several variables including the ratio of aqueous to non-aqueous manufacturing solvent phases and the concentration of surfactant employed. For example, the yield of aqueous core microcapsules with walls of piperazine arabate can be as high as 85% by volume. The volume yield of benzalkonium cellulose methylcarboxylate microcapsules can be as high as 40%.

Once encapsulated, core materials are protected from the environment, but water-soluble core materials may be slowly released from the microcapsules by suspending the capsules in an aqueous medium into which the core material can actively diffuse through the semipermeable microcapsule walls. In general, if one holds the nature of the wall-forming reactants constant one finds highly water-soluble materials are released more rapidly than are poorly water-soluble core materials and, in general, substances of low molecular weight are released more rapidly than are substances of higher molecular weight. Conversion of the microcapsules to lyocakes and resuspension in aqueous media is preferred.

The utility of these microcapsules as a sustained release device has been demonstrated with specific reference to a number of drugs such as the anti-asthmatic drug theophylline in a dialysis system. Others tested successfully include doxorubicin, niacinamide, deferoxamine and terbutaline. These are exemplified below with reference to theophylline.

An unexpected characteristic of the new microcapsules is the flexibility of the resulting microparticles when hydrated. This flexibility allows their passage without disruption through submicron filters routinely utilized for sterilization of solutions. Submicron filtration does not appear to change significantly the number or size distribution of the particle population.

Another unexpected property shown by microcapsules of this invention is their stability in water and their ability to encapsulate water. For example, the salt piperazine arabate, one of the preferred wall-forming components described herein, is itself soluble in water as may be shown by mixing stoichiometric volumes of aqueous solutions of piperazine and arabic acid. The piperazine arabate so formed is quite soluble and may be recovered as a brittle film from its aqueous solution by evaporation of the water and, if desired, again dissolved in water. However, when piperazine arabate is generated as an encapsulating membrane by the interfacial reaction of stoichiometric amounts of piperazine and arabic acid as taught herein, the resulting material is in a metastable, multi-lammelar form which is poorly soluble in water and which is capable of making stable encapsulations of water or aqueous solutions.

As a result, in contrast to the microcapsules of U.S. Pat. No. 3,959,457, the piperazine arabate microcapsules of this invention are stable in 80° C. water and in 0.1 N hydrochloric acid and 0.1 N sodium hydroxide.

EXAMPLE 1

1.0 g of arabic acid in 20 ml of water was dispersed in 25 ml of a vigorously stirred 10% solution of sorbitan trioleate in cyclohexane/chloroform (4:1).

While continuing to stir vigorously, 0.02 g of piperazine in 5 ml of cyclohexane/chloroform (4:1) was added to the dispersion. When the addition was completed, stirring was stopped and the vessel was sealed to prevent evaporation of the solvents. A milky suspension was observed. After 7 days, the sample was visually examined and found to contain the following settled percentage volumes of continuous organic, microcapsules and unencapsulated aqueous phases, respectively: 26, 73, 1.

In a similar manner, microcapsules were prepared at various ratios of aqueous to organic phase, ranging from 0.2 to 0.6 volume fraction aqueous phase.

| % Aqueous Phase | % Organic Phase | % Micro-capsules | % Unencapsulated Aqueous Phase | % Continuous Organic Phase |
|---|---|---|---|---|
| 20 | 80 | 33 | 0 | 67 |
| 30 | 70 | 49 | 0 | 51 |
| 40 | 60 | 73 | 1 | 26 |
| 50 | 50 | 85 | 5 | 10 |
| 60 | 40 | 85 | 8 | 7 |

EXAMPLE 2

The procedure of Example 1 was repeated for varying concentrations of sorbitan trioleate.

| % Sorbitan Trioleate | % Micro-capsules | % Unencapsulated Aqueous Phase | % Continuous Organic Phase |
|---|---|---|---|
| 0 | 2 | 32 | 66 |
| 5 | 52 | 5 | 43 |
| 10 | 68 | 2 | 30 |
| 15 | 72 | 0 | 28 |
| 20 | 71 | 0 | 29 |

EXAMPLE 3

Two aqueous solutions containing equal amounts of the drug theophylline were prepared. Solution A contained the drug microencapsulated following the teaching of this invention. In solution B the native drug was directly dissolved. Both solutions were dialyzed to determine the relative propensities of the encapsulated and unencapsulated drug to migrate from solution.

In the dialysis system the test solution is pumped in a continuous loop past a dialysis membrane at a constant flow rate. The same pump moves a continuous stream of aqueous recipient medium past the other side of the dialysis membrane and then to an automatic fraction collector. At timed intervals the fraction collector positions collection vessels for receipt of aliquots of dialysate from the recipient stream. Successive aliquots of recipient are analyzed spectrophotometrically for the concentration of released material in each.

These data showed that approximately 50% of the initial amount of unencapsulated theophylline was cleared from the donor stream in about 4 hours. However, microencapsulation controlled the release of theophylline so that only about 17% of the initial amount was released to the recipient stream in the same time period.

EXAMPLE 4

A solution of 0.05 g of sodium carboxymethylcellulose in 10 ml of water was dispersed in 35 ml of a vigorously stirred 10% solution of sorbitan trioleate in cyclohexane/chloroform (4:1).

While continuing to stir vigorously, 0.02 g of benzalkonium chloride in 5 ml of cyclohexane/chloroform (4:1) was added to the dispersion. When the addition was completed, stirring was stopped and the vessel was sealed to prevent evaporation of the solvents. A milky suspension was observed. After 7 days the sample was visually examined and found to contain the following settled percentage volumes of continuous organic, microcapsular and unencapsulated aqueous phases, respectively: 69, 27 and 4.

In similar manner, microcapsules were prepared at various ratios of aqueous to organic phase, ranging from 0.20 to 0.35 volume fraction aqueous phase.

| Preparation System | | Percentage Settled Volumes of Phases Resulting Products | | |
|---|---|---|---|---|
| Aqueous | Organic | Organic | Microcapsule | Aqueous |
| 20 | 80 | 69 | 27 | 4 |
| 23 | 77 | 60 | 36 | 4 |
| 26 | 74 | 58 | 38 | 4 |
| 29 | 71 | 52 | 40 | 8 |
| 31 | 69 | 55 | 35 | 10 |
| 33 | 67 | 60 | 20 | 20 |
| 35 | 65 | 60 | 10 | 30 |

While this invention has been described with reference to specific, and particularly, preferred embodiments thereof, it is not limited thereto and the appended claims are intended to be construed to encompass not only the specific forms and variants of the invention shown but to such other forms and variants as may be devised by those skilled in the art without departing from the true spirit and scope of the invention.

We claim:

1. A microcapsule comprising an aqueous core, and a capsular, ionically-stabilized, anisotropic Lewis salt membrane formed from the interfacial reaction product of an emulsion of an aqueous solution of a water-soluble, hydrophilic polymeric Lewis acid or salt thereof with a non-aqueous solution of a lipophilic Lewis base or salt thereof, wherein said Lewis base or salt thereof is selected from the group consisting of hexylamine, stearylamine, piperidine, triethylamine, hexanediamine, triethylenediamine, benzalkonium chloride, cetylpyridinium chloride, hexamethylrosanilium chloride and tetramethylrosanilium chloride.

2. A microcapsule of claim 1 in which the solvent of said non-aqueous solution is selected from cyclohexane, chloroform, n-butyl chloride, methylisobutyl ketone, chloroform/cyclohexane (1:4 vol%), dichloromethane/cyclohexane (1:4 vol %), and n-hexane/n-heptane (1:1 vol %).

3. A microcapsule of claim 1 in which the Lewis acid is selected from polyuronic acids and acidic resins.

4. A microcapsule of claim 1 in which the Lewis acid is selected from acacia, arabic acid, agar, carboxymethylcellulose, ghatti gum, guar gum, polyacrylic acid, polyacrylic acid/polyoxyethylene copolymer, and sterculia gum.

5. A microcapsule of claim 1 in which the Lewis acid salt is selected from sodium carboxymethylcellulose, sodium polyacrylate, sodium polyacrylate cross-linked with polyoxyethylene, and sodium alginate.

6. A microcapsule of claim 1 in which an active ingredient is dissolved or suspended within the aqueous core.

7. A microcapsule of claim 6 in which the active ingredient is FD & C Red No. 1, FD & C Red No. 40, or sodium fluorescein.

8. A microcapsule of claim 6 in which the active ingredient is a pharmaceutical.

9. A microcapsule of claim 8 in which the pharmaceutical is an anti-asthmatic or anti-neoplastic.

10. A microcapsule of claim 8 in which the pharmaceutical is selected from the group consisting of theophylline, doxorubicin, deferoxamine, and terbutaline.

11. A microcapsule comprising the ionically-stabilized, aniostropic Lewis salt reaction product of
   a) an emulsion of an aqueous solution of a polyfunctional Lewis acid or acid salt, a core material, an emulsifying agent, and a first non-aqueous solvent; and
   b) a polyfunctional Lewis base or basic salt dissolved in a second non-aqueous solvent soluble in said first non-aqueous solvent, wherein said Lewis base or salt thereof is selected from the group consisting of hexylamine, stearylamine, piperidine, triethylamine, hexanediamine, triethylenediamine, benzalkonium chloride, cetylpyridinium chloride, hexamethylrosanilium chloride and tetramethylrosanilium chloride.

12. A microcapsule of claim 11 in which said first and second non-aqueous solvents are the same.

13. A microcapsule of claim 11 in which the emulsifying agent is sorbitan trioleate.

14. A microcapsule of claim 11 in which the non-aqueous solvents are selected from cyclohexane, chloroform, n-butyl chloride, methylisobutyl ketone, chloroform/cyclohexane (1:2 vol %), dichloromethane/cyclohexane (1:4 vol %), and n-hexane/n-heptane (1:1 vol %).

15. A microcapsule of claim 11 in which the Lewis acid is selected from polyuronic acids and acidic resins.

16. A microcapsule of claim 11 in which the Lewis acid is selected from acacia, arabic acid, agar, carboxymethylcellulose, ghatti gum, guar gum, polyacrylic acid, polyacrylic acid/polyoxyethylene copolymer, and sterculia gum.

17. A microcapsule of claim 11 in which the Lewis acid salt is selected from sodium carboxymethylcellulose, sodium polyacrylate, sodium polyacrylate cross-linked with polyoxyethylene, and sodium alginate.

18. A microcapsule of claim 11 in which the core material is FD & C Red No. 1, FD & C Red No. 40, or sodium fluorescein.

19. A microcapsule of claim 11 in which the core material is a pharmaceutical.

20. A microcapsule of claim 19 in which the pharmaceutical is an anti-asthmatic or anti-neoplastic.

21. A microcapsule of claim 19 in which the pharmaceutical is selected from the group consisting of theophylline, doxorubicin, deferoxamine, and terbutaline.

22. A process for preparing aqueous core microcapsules having a capsular, ionically-stabilized, anisotropic Lewis salt membrane, comprising the steps of:
   a) dissolving a polyfunctional Lewis acid or salt thereof in water;
   b) dissolving or suspending a core material in water;
   c) emulsifying the solutions of steps a) and b) in a first non-aqueous solvent containing a surfactant to form an emulsion;
   d) dissolving a polyfunctional Lewis base or salt in a second non-aqueous solvent soluble in said first non-aqueous solvent, wherein said Lewis base or salt thereof is selected from the group consisting of hexylamine, stearylamine, piperidine, triethylamine, hexanediamine, triethylenediamine, benzalkonium chloride, cetylpyridinium chloride, hexamethylrosanilium chloride and tetramethylrosanilium chloride;
   e) adding the Lewis base solution to the emulsion, with stirring; and
   f) harvesting the microcapsules.

23. A process of claim 22 in which the non-aqueous solvents are selected from cyclohexane, chloroform, n-butyl chloride, methylisobutyl ketone, chloroform/cyclohexane (1:4 vol %), dichloromethane/ cyclohexane (1:4 vol %) and n-hexane/n-heptane (1:1 vol %)

24. A process of claim 22 in which the Lewis acid is selected from polyuronic acids and acidic resins.

25. A process of claim 22 in which the Lewis acid is selected from acacia, arabic acid, agar, carboxymethylcellulose, ghatti gum, guar gum, polyacrylic acid, polyacrylic acid/polyoxyethylene copolymer, and sterculia gum.

26. A process of claim 22 in which the Lewis acid salt is selected from sodium carboxymethylcellulose, sodium polyacrylate, sodium polyacrylate cross-linked with polyoxyethylene, and sodium alginate.

27. A process of claim 22 further comprising the steps of centrifuging to harvest the microcapsules, resuspending the microcapsules in a non-aqueous solvent, repeating the centrifuging/resuspending steps at least once, and lyophilizing the microcapsules.

28. A process of claim 22 in which the surfactant is from about 7% to about 20% sorbitan trioleate by volume of non-aqueous solvent.

29. A process of claim 22 in which the volume fraction of aqueous phase is from about 0.2 to about 0.6.

30. A process of claim 22 in which said first and second non-aqueous solvents are the same.

31. A process of claim 29 in which the Lewis base or salt thereof is first dissolved in the non-aqueous solvent and the remaining materials are emulsified therein.

* * * * *